United States Patent [19]

Milder et al.

[11] Patent Number: 5,045,051

[45] Date of Patent: Sep. 3, 1991

[54] LEAK DETECTOR

[75] Inventors: Fredric L. Milder, Brookline, Mass.; Saul Stricker, Richmond Hill, Canada

[73] Assignee: Abiomed, Inc., Danvers, Mass.

[21] Appl. No.: 323,322

[22] Filed: Mar. 14, 1989

[51] Int. Cl.$^5$ ............................................. A61B 19/00
[52] U.S. Cl. ........................................ 600/16; 600/18; 604/67; 604/96; 606/192; 606/194
[58] Field of Search ..................... 600/16, 18; 604/67, 604/96, 100; 606/192, 194

[56] References Cited

U.S. PATENT DOCUMENTS

| | | | |
|---|---|---|---|
| 3,720,199 | 3/1973 | Rishton et al. | 604/100 |
| 4,162,543 | 7/1979 | Shumakov et al. | 600/16 |
| 4,465,063 | 8/1984 | Nielsen et al. | 600/16 |
| 4,846,831 | 7/1989 | Skillin | 600/16 |
| 4,861,330 | 3/1987 | Voss | 606/194 |

FOREIGN PATENT DOCUMENTS 0247015  11/1987  European Pat. Off. ............. 600/16

Primary Examiner—Lee S. Cohen
Assistant Examiner—John D. Zele
Attorney, Agent, or Firm—Lahive & Cockfield

[57] ABSTRACT

A system for detecting leakage in a device having a fluid-driven membrane inserted in the body, for example, a balloon pump, includes a fluid drive circuit with a moisture remover having a capacity just sufficient to remove water vapor entering the circuit due to intrinsic permeability of the membrane. An in-line humidity sensor responds quickly to an increase in vapor pressure, indicating a leak, and activates a shut-down circuit to prevent leakage of the drive fluid into the body. The system is employed in a balloon pump driven by a pulsating air source.

9 Claims, 2 Drawing Sheets

LEAK DETECTOR

BACKGROUND

This invention relates to cardiac assist devices which are placed within the body, or in the blood stream, and driven by a source of fluid such as air, helium or carbon dioxide. It is of particular relevance to temporary devices for insertion in the vascular system, such as intraaortic balloon pumps and the like, which have a balloon or bladder formed of a thin membrane.

It is necessary in devices of this type to guard against leakage of the drive fluid through tears or cracks in the balloon membrane. Current methods of leak detection rely on detecting changes in gas pressure in the closed fluid drive system while the pump is in operation. One problem with this method is the relatively low sensitivity of the technique, which can detect gas leaks of about 3 cc/minute. Considering that hundreds of small gas bubbles may be formed in the bloodstream for each cubic centimeter of gas leakage through a small hole, this detectable leakage threshhold may be seen to pose a significant risk for the patient. It is therefore desirable to detect leakage of the fluid system faster or with greater sensitivity.

SUMMARY OF THE INVENTION

It is an object of the invention to provide a system which quickly and reliably detect leaks in a fluid-driven cardiac assist device.

In accordance with the present invention, an improved leak detection system includes a sensor in the fluid drive circuit which detects a partial pressure of water vapor in the drive fluid. A pulsating pressure source is connected by a conduit to a balloon or fluid-driven membrane, which pumps blood by repetitive inflation/deflation cycles, and a moisture remover is connected to the conduit to remove moisture from the drive fluid. The moisture remover has a capacity to remove moisture at a rate comparable to the intrinsic influx of moisture due to permeability of the pump membrane, thus maintaining moisture at a low constant or slowly varying level. When a leak occurs, the influx of moisture from the bloodstream into the balloon or conduit quickly raises the partial pressure of water in the drive fluid, which is detected by the sensor.

In a presently preferred embodiment, the moisture remover is a thermoelectrically cooled condensation trap located in the fluid path between the drive source and the balloon membrane. The surface area of a cooled condensation wall is selected to achieve a removal rate which normally maintains a uniform low humidity in the conduit. Preferably the moisture sensor is located between the trap and the membrane, so that it receives a flow of warmed fluid fresh from the balloon, alternately with a flow of fluid, in the reverse direction, which has passed the moisture removing trap.

BRIEF DESCRIPTION OF THE DRAWINGS

These and other features of the invention will be understood from the following description of illustrated embodiments, taken together with the drawings, wherein.

DETAILED DESCRIPTION

Figure 1:
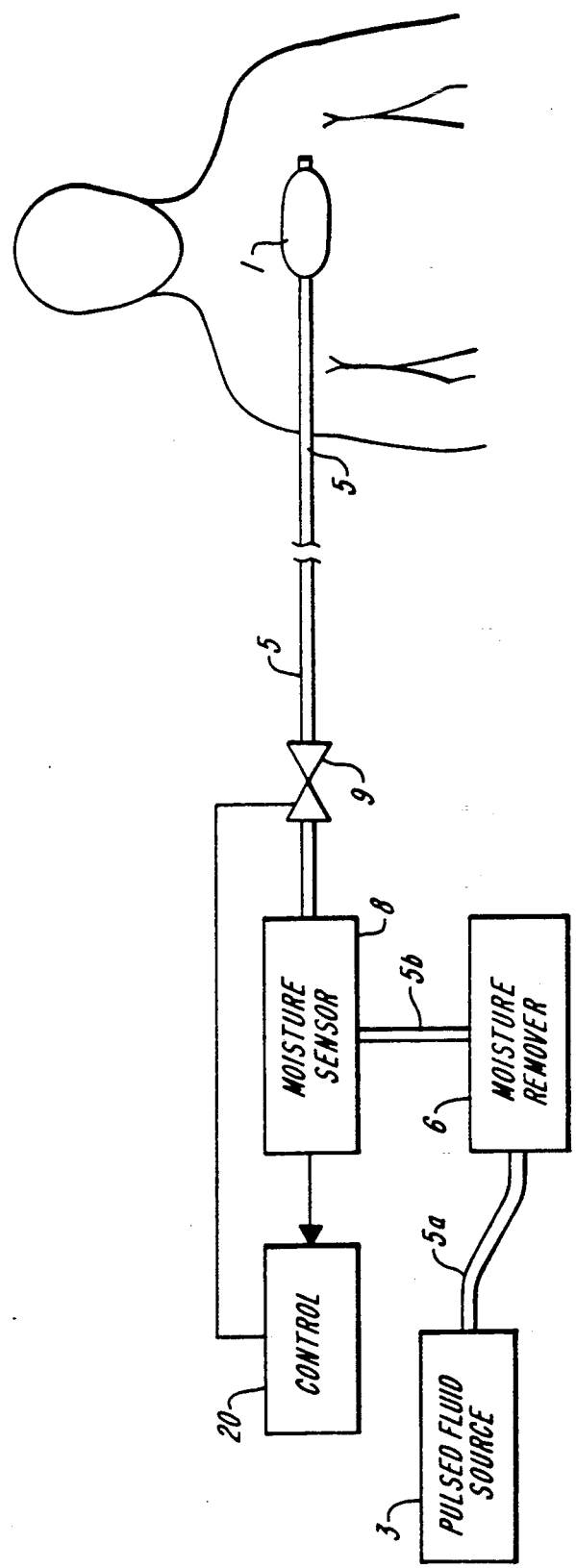
FIG. 1 is a schematic diagram of a system including a leak detector according to the present invention.

A system including a leak detector is schematically illustrated in FIG. 1. In this system, a balloon 1, which may, for example, be inserted through a blood vessel into the aorta, is connected by a conduit 5 to a pulsed fluid source 3 so that it is repetitively inflated and deflated to provide a blood pumping action. There is thus a back-and-forth flow of fluid, e.g., helium or carbon dioxide, between balloon 1 and source 3. According to a broad aspect of the invention, a moisture remover 6 is placed in the fluid drive circuit 1,3,5 to maintain a relatively stable humidity level, and a moisture sensor 8 detects fluctuations in humidity indicative of leakage of biological fluid into the system. When a high humidity is detected a controller 20 shuts a valve 9 to prevent gas from leaking into the bloodstream.

The pulsed fluid source 3 may be, for example, a solenoid- or motor-driven assembly which cyclically produces a positive and negative pressure to drive the balloon. The timing and drive stroke are adjusted by sensors and control circuitry known in the art to synchronize the balloon action with the biological cardiac pumping action and available blood volume. The moisture remove 6 may be a cold trap, as described further below.

The leak detection system of the present invention relies on the premise that if a balloon has a sufficiently large hole in it, biological fluid will enter the balloon from the bloodstream, and the water from the fluid will evaporate and increase the relative humidity of the driving gas within the conduit. If the capacity of the cold trap is selected to be just sufficiently high to keep up with the rate of vapor diffusion across the pump membrane, then any increase in the rate of moisture generation within the drive system above this basic membrane permeability rate "overloads" the cold trap, and the relative humidity quickly increases. A sensor monitors the relative humidity in the drive line to detect an increase in humidity. The response of an appropriately chosen sensor may exhibit greater sensitivity than the pressure monitor conventionally employed to measure leakage.

This leak detection system responds only to those leaks which allow biological fluid to enter the gas drive circuit. The system relies on the difference in the rate of vapor production between diffusion through the balloon and evaporation of the water vapor from blood within the balloon.

Typically, the rate of moisture entry due to transmembrane diffusion is small. For a polyurethane film such as used in an intraaortic balloon pump (IABP), at 38° C., the diffusion rate is 15.7–29.5 mm/m$^2$·24hr. For a (0.127) mm thick balloon membrane having a surface area of $75 \times 10^{-4}$ m$^2$, the rate of moisture migration via diffusion is therefore:

$$\text{Moisture migration in grams} = \frac{\text{permeability} \times \text{area} \times \text{time}}{\text{thickness}} =$$

$$\frac{15.7 \times 75 \times 10^{-4} \times 1}{0.127} = 0.93 \text{ grams per day.}$$

or expressed per second, $1.08 \times 1^{-5}$ grams per second.

Thus, a cold trap capable of removing vapor at a rate slightly above $1.08 \times 10^{-5}$ g/sec will maintain the base moisture load of the system low. For different size balloons, or different membrane materials, the rate of ingress of moisture is calculated or measured, and the moisture remover is sized to provide a stable, i.e., a low constant or slowly-varying, level of moisture within the system. Any water entering the system that results in substantial additional vapor production then quickly "overloads" the cold trap removal capacity and results in a build-up of higher relative humidity within the gas circuit. Since a grossly oversized cold trap would remove moisture from the gas as quickly as it was generated, and not allow the relative humidity to increase, the capacity of the cold trap is selected to be not significantly greater than the normal moisture influx due to permeabilty of the membrane.

The normal permeability influx is thus measured for the pump device, and the cold trap is selected accordingly.

Figure 2:
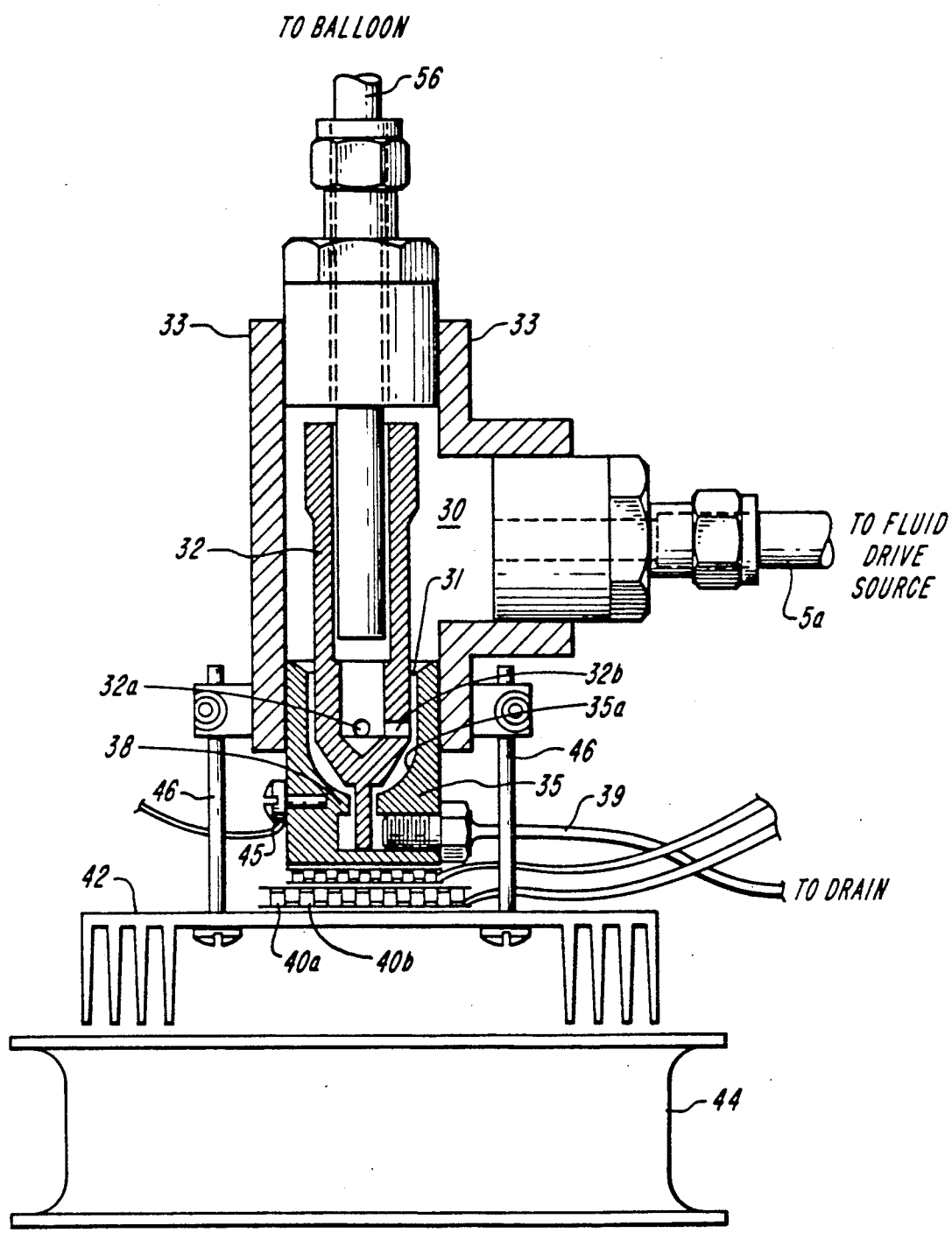
FIG. 2 is a cross-sectional view of a presently preferred embodiment of a leak detector.

In one embodiment, shown in cross-section in FIG. 2, the moisture remover 6 is a cold trap with a cup-shaped condensation surface against which the drive gas is directed during the deflation and inflation portions of the fluid drive pulse. The surface condenses excess moisture and directs it to a drain. The moisture removal capacity of this device is determined primarily by the condensation surface temperature and the area of the condensation surface and, to a lesser extent, the efficiency with which the pulsating drive gas is directed against the surface.

In this embodiment, a source conduit 5a connects a transfer chamber 30, defined by a plastic T housing 33, to the drive gas source 3 (FIG. 1), and the chamber 30 communicates with the balloon via an annular passage 31 defined between a condensation cup 35 and a filler piece 32. Filler piece 32 serves as a termination nozzle for a conduit 5b which leads to the balloon.

The diameter of filler piece 32 is such that the annular space 31 effectively channels gas passing between chamber 30 and conduit 5b into contact with the surrounding condensation cup 35 at its inner surface 35a. Radially directed apertures 32a, 32b direct gas returning from the balloon at the condensation surface 35a. The cup 35 curves downward to an opening 38 through which condensate flows to a small bore drain tube 39, which may be periodically drained to assure that accumulated moisture does not revaporize or remain in the system.

The condensation cup 35 is preferably formed of a highly heat conductive material, such as aluminum or copper, and maintained at a fixed temperature slightly above freezing, e.g., 5° C., by a plurality of thermoelectric cooling devices 40a, 40b . . . . A heat sink 42 contacts the hot side of the devices 40a, 40b . . . , and a muffin fan 44 maintains the heat sink at approximately room temperature. A temperature sensor 45, such as a solid state sensor or thermocouple, provides an indication of the temperature of the trap, and a thermostatic control system controls power provided to the cooling devices 40a, 40b . . . to maintain the trap at the desired temperature. The cooled body of the trap is mounted on thermally insulating stand-offs 46 to isolate it from the heat sink.

Preferably, the partial pressure of water vapor in the gas of the drive system is measured in conduit 5b, by placing a relative humidity sensor in the gas stream. A sensor is preferably employed having a response time of several seconds or less, and having little or no drift in calibration over time. A suitable device is available from Ohmic Instruments, of St. Michaels, Md., as one of their "MHS" series of humidity sensors. These sensors change their AC conductivity as a function of relative humidity, and are characterized by a response time of about three seconds, with very stable characteristics over time. The moisture sensor 8 as well as the moisture remover 6 are each preferably located within the drive console (not shown) which houses the pulsed fluid source 3. The sensor is preferably placed as close as possible to the catheter so that it is exposed to warm gas returning from the balloon before the gas has gone through the cold trap.

Specifically, during balloon inflation phase of the drive system cycle, the gas flows through the cold trap, past the humidity sensor, and into the catheter-balloon assembly. During deflation phase of the drive system cycle, the somewhat more moisture-laden and warmer gas returns past the sensor, and through the cold trap, where some moisture condenses out. Since the response time of the sensor is longer than the typical cycle rate of such a drive system, the output of the sensor corresponds to an intermediate relative humidity value between the cool, dry gas going into the balloon, and the warmer, more humid gas returning. A blood leak into the balloon leads to rapid increase in humidity in the drive system, due to the rapid evaporation rate of warm fluid and to the limited moisture removal rate of the critically-sized cold trap. The rise of relative humidity above a predetermined value is an indication of the existence of a leak, which triggers an automatic safety shut-down system. The sensor may also be used, ex vivo, to test the balloon integrity prior to use.

It will be appreciated that the illustrated cold trap moisture remover 6 provides a structure which is readily matched to the intrinsic moisture permeability of a balloon, and which effectively maintains a low moisture level in the functioning system while directing condensate away from those system components which are adversely affected by condensation. The system architecture results in a rapid elevation of relative humidity when defects of the balloon permit entry of blood or fluids, and the moisture sensor readily detects this condition.

It will be understood that while the cold trap has been described as critically-sized, in the sense that it is just sufficient to remove moisture due to the intrinsic permeability of the membrane, the critical limitation is that the trap be at least sufficient to remove the intrinsic moisture, but that it be ineffective to remove the amount of moisture due to a medically significant leak. Because of the normal variations in balloon permeability, and the fairly large difference between the normal and leakage rates, the cold trap may as a practical matter have a capacity several to ten times larger than the intrinsic permeability rate.

As indicated in the schematic of FIG. 1, a safety control 20 closes valve 9 when a dangerous humidity indication is sensed. Preferably, valve 9 is an electrically controlled, normally closed valve, and control 20 cuts the power upon detecting a leak condition, thus providing a fail-safe mode of shut down. The valve de-actuation is synchronized with the deflation stroke of the drive pulse, so that the balloon is shut down in its deflated, negative pressure, state. Other aspects of device shut down procedures known in the art are, of course, observed.

The invention being thus described, other forms and variations will occur to those skilled in the art and all such forms and variations are considered to be within the scope of the invention, as defined by the claims appended hereto.

What is claimed is:

1. A system for leak detection in a blood pump having a pumping membrane located within a body and a fluid drive conduit extending from the pumping membrane to a drive source, such system comprising moisture remover means for fluid communication with the conduit having a capacity for removing just sufficient moisture to maintain a stable water vapor pressure in the conduit due to intrinsic permeability of said pumping membrane located within the body and communication with the conduit, and humidity detector means in fluid communication with said conduit for monitoring humidity, whereby an increase in water vapor pressure provides an indication of membrane leakage.

2. A system according to claim 1, wherein the pumping membrane includes a balloon and the drive source includes a pulsatile fluid pressure source connected in a closed fluid system via the fluid drive conduit with the balloon and said humidity detector means is adapted to be located between the moisture remover means and the balloon.

3. A system according to claim 1, wherein the moisture remover means is a condensation-type moisture remover means.

4. A system according to claim 3, wherein the moisture remover means is a thermoelectrically-cooled cup having a surface area of a size effective to condense moisture at a rate corresponding to entry of moisture due to permeability of the pumping membrane.

5. A system according to claim 4, wherein the humidity sensor means is a solid state sensor.

6. A system according to claim 1, wherein the membrane is a balloon membrane and the pump is an intra-aortic balloon pump and the moisture remover means has a removal capacity rate between one and ten times the intrinsic permeability of the balloon membrane.

7. A method for detecting a leak in a fluid drive circuit of a fluid driven membrane blood pumping system having a pumping membrane located within a body, such method comprising the steps of providing a moisture remover having a moisture removal capacity rate approximately just sufficient to remove moisture entering the fluid drive circuit due to intrinsic permeability of the pumping membrane, and providing a moisture sensor in fluid communication with the fluid drive circuit, whereby leakage of fluid greater than the intrinsic permeability of the pumping membrane is detected by the moisture sensor as an increase in humidity in said circuit.

8. The method of claim 7, wherein said fluid drive circuit is a pulsed pressure fluid drive circuit comprising a pumping unit including said pumping membrane, and a drive fluid line for carrying drive fluid returning from said pumping membrane, and wherein the step of providing a moisture remover includes providing a moisture remover in said drive fluid line.

9. The method of claim 8, wherein the step of providing a moisture sensor includes locating the moisture sensor in said line between the moisture remover and the pumping membrane.

* * * * *